(12) United States Patent
Angeletakis

(10) Patent No.: US 10,307,345 B2
(45) Date of Patent: Jun. 4, 2019

(54) HYDROPHILIC IMPRESSION MATERIAL WITH IMPROVED STORAGE STABILITY

(71) Applicant: Christos Angeletakis, Bear, DE (US)

(72) Inventor: Christos Angeletakis, Bear, DE (US)

(73) Assignee: DENTSPLY SIRONA Inc., York, PA (US)

( * ) Notice: Subject to any disclaimer, the term of this patent is extended or adjusted under 35 U.S.C. 154(b) by 0 days.

(21) Appl. No.: 15/341,325

(22) Filed: Nov. 2, 2016

(65) Prior Publication Data

US 2017/0296443 A1  Oct. 19, 2017

Related U.S. Application Data

(60) Provisional application No. 62/249,509, filed on Nov. 2, 2015.

(51) Int. Cl.
| | |
|---|---|
| *A61K 6/10* | (2006.01) |
| *C08L 83/04* | (2006.01) |
| *C08L 83/12* | (2006.01) |
| *C08K 5/06* | (2006.01) |
| *C08K 3/36* | (2006.01) |
| *A61K 6/00* | (2006.01) |

(52) U.S. Cl.
CPC .............. *A61K 6/10* (2013.01); *A61K 6/0047* (2013.01); *C08K 3/36* (2013.01); *C08K 5/06* (2013.01); *C08L 83/04* (2013.01); *C08L 83/12* (2013.01)

(58) Field of Classification Search
CPC ....................................................... A61K 6/10
See application file for complete search history.

(56) References Cited

U.S. PATENT DOCUMENTS

| 4,657,959 | A | * | 4/1987 | Bryan | ...................... A61K 6/10 264/16 |
|---|---|---|---|---|---|
| 6,121,362 | A | * | 9/2000 | Wanek | ...................... A61K 6/10 523/109 |
| 7,812,065 | B2 | * | 10/2010 | Bublewitz | ................ A61K 6/10 106/35 |
| 8,466,210 | B2 | * | 6/2013 | Zech | ...................... A61K 6/083 522/148 |
| 8,916,623 | B2 | * | 12/2014 | Riedel | ...................... A61K 6/10 106/35 |
| 2005/0181324 | A1 | * | 8/2005 | Hare | ........................ A61K 6/10 433/48 |
| 2012/0077900 | A1 | * | 3/2012 | Maurer | .................. A61K 6/083 523/109 |

FOREIGN PATENT DOCUMENTS

WO    WO 2004/058196    *    7/2004

* cited by examiner

*Primary Examiner* — Marc S Zimmer
(74) *Attorney, Agent, or Firm* — Dentsply Sirona Inc.

(57) ABSTRACT

Disclosed herein is a dental impression material that includes a two part addition curing silicone composition. The disclosed impression material contains a surfactant system composed of a fluorosurfactant and a fatty alcohol ethoxylate. The impression material disclosed herein exhibits improved storage stability than known systems using fluorosurfactants and silicone ether compounds.

4 Claims, No Drawings

HYDROPHILIC IMPRESSION MATERIAL WITH IMPROVED STORAGE STABILITY

FIELD OF THE INVENTION

Disclosed herein is a two part addition curing silicone composition is presented usable as a dental impression material. The disclosed impression material contains a surfactant system composed of a fluorosurfactant and a fatty alcohol ethoxylate that has better storage stability than known systems using fluorosurfactants and silicone ether compounds.

BACKGROUND OF THE INVENTION

In dentistry, addition silicones are the most widely used impression materials. Addition curing silicones are favored as impression materials in dentistry for their high accuracy and dimensional stability.

In U.S. Pat. No. 4,675,959 the use of various surfactants is described, some being the fluoroalkyl polyoxyethylene type. However, no combinations of surfactants are described.

U.S. Pat. No. 6,291,546 describes the use of nonionic surfactants of two types, specifically alkyl ethers and fluoroalkyl ethers like the Zonyl 100 (Dupont) type.

U.S. Pat. No. 7,812,065 describes a combination of a fluoroalkyl ether with a silicone ether defined as "a non-ionic surfactant with a molecular mass of less than 6000 g/mol containing at least one (poly)alkylene oxide group as well as one silicon containing group". This combination is claimed to give a low contact angle on mixing but not on cured impression material.

U.S. Pat. No. 8,466,210 describes the use of a perfluorinated polyether used in combination with a silicone ether to afford a low contact angle for mixed but not yet cured impression material.

U.S. Pat. No. 8,916,623 describes the use of nonionic surfactants of three types: polyoxyethylene alkyl ethers, silicone alkyl ethers and fluoroalkyl ethers like the Zonyl 100 (Dupont) type. The polyoxyethylene alkyl ethers described therein are end-capped with alkyl groups and do not contain any terminal hydroxyl groups. Combinations of these three surfactant types is reported to give a low contact angle on mixed but not yet cured impression material.

It is necessary, in effectively taking an impression, to be able to easily remove the impression from the dentition without tearing, particularly at thin marginal areas, to preserve fine detail and this property is usually evaluated by measuring tear strength. Linear divinyl PDMS are used in commercial addition silicone based impression materials. U.S. Pat. No. 56,661,222 describes an addition silicone impression material based on quadri-functional polydimethylsiloxane (PDMS) or QM resins. The use of these QM resins provides improved tear strength to the polymerized impression composition by increasing its resulting polymerized crosslink density.

There is a need of an impression material that exhibits a low contact angle before set with adequate tear strength. Moreover this impression material needs to have adequate shelf life stability to be usable upon at least 3 years of storage at room temperature. This can be shown by an accelerated aging test.

SUMMARY

Disclosed here in is an impression material formulation having high tear strength as defined by a tear strength value of at least about 270 PSI that exhibits a CA of lower than 20 degrees 30 seconds after mixing. The low contact angle is accomplished via a combination of surfactants that leads to increased stability of the paste. These surfactants are selected from:
  a) a group of non-ionic fluorosurfactants,
  b) and from the group consisting of monofunctional alcohol alkoxylates, preferably ethoxylated C10-C16 alcohols, propoxylated C10-C16 alcohols, or ethoxylated propoxylated C10-C16 alcohols, and the above two surfactants are mixed in a two part addition silicone formulation preferably containing in the majority QM siloxanes for increased tear strength upon curing.

DETAILED DESCRIPTION

However due to the hydrophobic nature of siloxanes, surfactants need to be included to make sure the wettability is adequate for a good impression. This is because addition of surfactants improves the ability of the impression material to displace oral fluids during curing. Wettability or hydrophilicity of an impression material is usually characterized by a contact angle method. This is accomplished by taking contact angle measurements of water droplets on their surface after mixing before and after cure. A contact angle (CA) below 90 degrees is desirable for a hydrophilic material and especially useful are materials that have a CA below 20 degrees before setting.

Addition curing silicones cure with a hydrosilation mechanism and contain a platinum compound as a catalyst. Addition of surfactants however in the addition curing silicone formulations usually results in the reduction of curing speed and/or physical properties. This occurs because the polar groups in the surfactants are capable to coordinate with the platinum catalyst and rendering it inactive for the addition reaction that leads to curing of the material. So the concentration of surfactant used needs to be minimized to reduce platinum demand and enhance physical properties.

The surfactants used with addition silicones are usually of the non-ionic type to enhance compatibility with the siloxane hydrophobic matrix. One such type are silicone ethers where the hydrophobic fragment of the surfactant is a siloxane, usually a trisiloxane.

These silicone ethers are usually prepared by the platinum complex catalyzed hydrosilation reaction of hydride functionalized dimethylsiloxanes with alkenes and contain Si—C—C linkages. There are several commercially available such silicone ethers such as the Masil types or the Silwet series from Momentive. There are many diverse uses for these compounds, such as nonionic surfactants and defoamers. However the preparation method used for these, namely hydrosilation, suffers from the disadvantage that it never goes to completion, always resulting in the starting materials being present in the final product, especially the alkene reactant in non-negligible amounts, e.g., at 10% or higher, and other unsaturated impurities such as enol ethers. These impurities are difficult to remove by distillation due to high boiling point. These impurities interfere with the curing of the impression material particularly if they are included in the same side as the platinum catalyst. It is advantageous to include the surfactants on both sides in order to get a more uniformly mixed paste upon mixing.

Alkoxy ether non-ionic surfactants are not prone to the problems of the silicone ethers since they can be obtained in higher purity.

The impression material disclosed herein is a two part (catalyst and base) addition silicone composition. This composition comprises: (1) a curable organopolysiloxane polymer, preferably a polydimethyl siloxane (PDMS) terminated in at least two vinyl groups and most preferably a polydimethyl siloxane (PDMS) terminated in four vinyl groups, (2) an organopolysiloxane compound capable of crosslinking said curable organopolysiloxane polymer preferably a hydride functional polydimethylsiloxane or PDMS hydride of a minimum 1.0 mmol Hydrogen per gram, (3) a catalyst for enabling the addition polymerization reaction preferably Karstedt's catalyst, (4) at least one filler, and (5) a combination of surfactants to improve the hydrophilicity or wettability of the system. The catalyst part comprises (1), (3), (4) and (5) while the base part comprises (1), (2), (4) and (5).

The first type of nonionic surfactant useful herein is a fluoroaliphatic polyoxyethylene type surfactant, examples of commercially available fluoroaliphatic polyoxyethylene type surfactants include Masurf 2800 (a perfluoroalkyl oxyethylene adduct by Emerald Corp.), Fluorad FC-170-C (a perfluoroalkylsulfonamido oxyethylene adduct By 3M Corp.), Zonyl FSH (Dupont Corp.), and Fluowet OTN (Clariant Co.). Preferred surfactants include those containing a C6 perfluorinated aliphatic chain bonded to a polyoxyethylene fragment giving an overall molecular weight range of 400 to 800 and preferably approx. 600, such as Masurf 2800 with an approximate structure shown below.

The second type of nonionic surfactant used herein is a monofunctional alcohol alkoxylate type surfactant. These can be the reaction product of a higher linear alcohol and a mixture of ethylene and propylene oxides, containing a mixed chain of ethylene oxide and propylene oxide, terminated by a hydroxyl group and are characterized as being low foaming. Examples include Type A (a C13-C15 fatty alcohol condensed with 6 moles ethylene oxide and 3-4 moles propylene oxide), Type B (a C13-C15 fatty alcohol condensed with 7 mole propylene oxide and 4 mole ethylene oxide), and Type C (a C13-C15 fatty alcohol condensed with 5 moles propylene oxide and 10 moles ethylene oxide). Type A, where m+n=about 9 to 10 and molecular weight is approx. 640 are suitable due to its lower molecular weight and therefore increased mobility in the resin matrix. Examples are Plurafac RA 300 (BASF), Berol 185 (AkzoNobel), Antarox LF 45 (Rhodia) and have a general formula of:

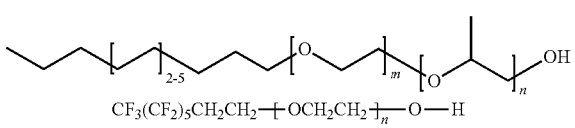

$$CF_3(CF_2)_5CH_2CH_2\text{---}[OCH_2CH_2]_n\text{---}O\text{---}H$$

Where n is from 5 to 7.

Test Methods

Tear Strength:

Test was performed in an I shaped cavity mold as described in U.S. Pat. No. 5,661,222.

Work Set Time:

ADA Specification 19: Non-Aqueous Elastomer Impression Materials (1976, as amended in 19a of 1982).

Contact Angle:

Dynamic contact angle measurements were performed using the Kruss DSA 100 Contact Angle Instrument or goniometer (manufactured by Kruss, Hamburg, Germany) equipped with an automatic measuring system and a humidity chamber at 80% relative humidity and a constant temperature of 25 C. The base and catalyst were extruded through a 50 ml Mixpac double barreled cartridge and a mixing tip onto a metal mold with a 0.20 mm thick cavity and brought to a thickness of 0.20 mm using a razor blade. At 30 seconds after the start of mixing a drop of water, 6 μl in volume was applied to the surface of the curing material and the contact angle was determined dynamically at the specified times using the video camera at 25 frames per second and calculated using the standard software of the instrument.

Example Formulation

A formulation example is described below. A Base Component A and a Catalyst Component B was prepared using the ingredients shown in Table 1. Mixing of each component's ingredients is done in a double planetary mixer having a mixing pot heated with circulating water at 45-50 C. and under 65 mm of mercury vacuum.

TABLE I

Base and Catalyst Component Pastes Composition.

|  | Component A (Base) | Component B (Catalyst) |
|---|---|---|
| PDMS Hydride | 8 | 0 |
| 200 csk divinyl PDMS | 2 | 2 |
| (5000-7000 cps) QM resin dispersion | 38.8 | 47.7 |
| (45000-60000 cps) QM resin dispersion | 14 | 14 |
| Cristobalite | 24 | 26 |
| Cab-O-Sil TS-530 fumed silica | 4 | 4 |
| Sodium Aluminum silicate | 5 | 5 |
| Platinum Catalyst 2% | 0 | 0.5 |
| Platinum on Calcium Carbonate | 0 | 0.1 |
| Pigments dispersed in divinyl PDMS | 4 | 0 |
| Peppermint Oil | 0.2 | 0.2 |
| Total | 100 | 100 |

These components then were diluted with the surfactants disclosed herein in the ratios shown in Table 2 using a planetary mixer.

TABLE 2

Composition of Catalyst and Base Pastes.

| Paste | Catalyst 8 | Catalyst 9 | Catalyst 10 | Catalyst 11 | Base 3 | Base 4 | Base 7 |
|---|---|---|---|---|---|---|---|
| Component A (Base) | 0 | 0 | 0 | 0 | 92 | 92 | 93 |
| Component B (Catalyst) | 98 | 98 | 97 | 97 | 0 | 0 | 0 |
| Silicone Ether* | 2 | 0 | 3 | 0 | 1 | 1 | 1 |
| Alkoxylated | 0 | 2 | 0 | 3 | 0 | 1 | 0 |

TABLE 2-continued

Composition of Catalyst and Base Pastes.

| Paste | Catalyst 8 | Catalyst 9 | Catalyst 10 | Catalyst 11 | Base 3 | Base 4 | Base 7 |
|---|---|---|---|---|---|---|---|
| Alcohol** | | | | | | | |
| Fluorosurfactant | 0 | 0 | 0 | 0 | 7 | 7 | 7 |
| Total | 100 | 100 | 100 | 100 | 100 | 100 | 100 |

*Silicone ether is Masil SF19 (Emerald Chemicals),
**Alkoxylated alcohol is Plurafac RA 300 (BASF)

The following combinations of Base/Catalyst pastes were tested for work and set time, tear strength and contact angle.

TABLE 3

Properties of Base/Catalyst combinations.

| Base/Catalyst Combination | 3/8 | 4/9 |
|---|---|---|
| Work Time (sec) | 225 | 220 |
| Set Time (sec) | 585 | 540 |
| % Silicone Ether | 3 | 0 |
| % Alkoxylated Alcohol | 0 | 3 |
| % Fluorosurfactant | 7 | 7 |
| Tear Strength (SD) psi | 274(11) | 248 (5) |
| Contact angle at 1 sec | 11 | 15 |
| Contact angle at 2 sec | 8 | 13 |
| Contact angle at 5 sec | 6 | 11 |

The accelerated stability testing of some of the Base/Catalyst combinations at 60 C are shown in Table 4. This testing was performed according to the guidelines of ASTM F1980 07(2011) "Standard Guide for Accelerated Aging of Sterile Barrier Systems for Medical Devices".

TABLE 4

Stability Testing at 60 C Using Catalysts with Low Pt Content

| Base/Catalyst Pair tested | Alkoxylated Alcohol | Silicone Ether | 60 C Storage time (weeks) | WORK TIME sec | SET TIME sec |
|---|---|---|---|---|---|
| 3/8 | None | Both Sides equally | 0 | 225 | 585 |
| 7/10 | None | Catalyst side Only | 0 | 250 | 660 |
| 4/9 | Both Sides equally | None | 0 | 220 | 540 |
| 7/11 | Catalyst side Only | None | 0 | 240 | 585 |
| 3/8 | None | Both Sides | 1 | 255 | 660 |
| 7/10 | None | Catalyst side Only | 1 | 330 | 720 |
| 4/9 | Both Sides equally | None | 1 | 195 | 450 |
| 7/11 | Catalyst side Only | None | 1 | 240 | 570 |
| 3/8 | None | Both Sides equally | 2 | 305 | 780 |
| 7/10 | None | Catalyst side Only | 2 | 365 | 780 |
| 4/9 | Both Sides equally | None | 2 | 200 | 475 |
| 7/11 | Catalyst side Only | None | 2 | 265 | 660 |
| 3/8 | None | Both Sides equally | 4 | >30 min | No Set |
| 7/10 | None | Catalyst side Only | 4 | >20 min | No Set |
| 4/9 | Both Sides equally | None | 4 | 465 | >20 min |
| 7/11 | Catalyst side Only | None | 4 | 600 | 30 min |

From these results it can be seen that in an addition silicone impression formulation the use of a combination of the surfactants described in this invention, namely a fluorosurfactant of the fluoroaliphatic polyoxyethylene type together with a monofunctional alcohol alkoxylate affords a desirable low contact angle with water on mixed but not yet cured impression material. Moreover such formulations are stable in an accelerated aging test suggesting longer shelf life time. In comparison formulations including a silicone ether as exemplified by Masil SF 19 give prolonged setting times upon aging gradually leading to not setting at all when evaluated in an accelerated aging test.

I claim:

1. An impression material comprising a catalyst part and a base part,
    the catalyst part comprises a curable organopolysiloxane polymer, a catalyst, at least one filler and at least one surfactant,
    the base part comprises a curable organopolysiloxane polymer, an organopolysiloxane compound capable of crosslinking said curable organopolysiloxane polymer, at least, one filler and a combination of surfactants;
    wherein the at least one surfactant of the catalyst part includes a monofunctional alcohol alkoxylate type surfactant;
    wherein the combination of surfactants of the base part includes any combination of a silicone ether, a fluoroaliphatic polyoxyethylene type surfactant, and a monofunctional alcohol alkoxylate type surfactant;
    wherein the fluoroaliphatic polyoxyethylene type surfactant is a C6 perfluorinated aliphatic chain bonded to a polyoxyethylene fragment giving an overall molecular weight range of from 400 to 800; and
    wherein the monofunctional alcohol alkoxylate type surfactant is

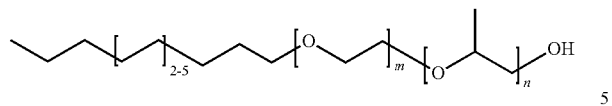

wherein the sum of m and n is 9 or 10.

2. The impression material according to claim 1, wherein the at least one surfactant of the catalyst part and one of surfactant of the combination of surfactants of the base part are the same.

3. The impression material according to claim 1, wherein the at least one surfactant of the catalyst part and the combination of surfactants of the base part are different.

4. The impression material according to claim 1, wherein the fluoroaliphatic polyoxyethylene type surfactant is

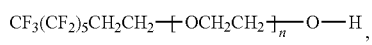

wherein n is from 5 to 7.

* * * * *